United States Patent [19]

Huang

[11] Patent Number: 4,971,827

[45] Date of Patent: Nov. 20, 1990

[54] METHOD OF PRODUCING CHOLESTEROL-FREE EGG PRODUCTS WITH AN EXTENDED REFRIGERATED SHELF LIFE AND PRODUCTS PRODUCED THEREBY

[75] Inventor: Frank Huang, Worthington, Ohio

[73] Assignee: Specialty Foods Investement Company, Wilmington, Del.

[21] Appl. No.: 495,000

[22] Filed: Apr. 19, 1990

Related U.S. Application Data

[63] Continuation of Ser. No. 7,209,802, Jun. 22, 1988, abandoned.

[51] Int. Cl.$^5$ ................................................. A23L 3/00
[52] U.S. Cl. ..................................... 426/614; 426/521; 426/399
[58] Field of Search ....................... 426/614, 526, 399

[56] References Cited

U.S. PATENT DOCUMENTS 4,808,425 2/1989 Swartzel .............................. 426/399

Primary Examiner—Jeanette Hunter
Attorney, Agent, or Firm—John L. Gray

[57] ABSTRACT

A process and product produced thereby which involves subjecting an egg white product to turbulent flow at an elevated temperature not to exceed 162° F. for a period of time not to exceed one minute followed by immediate rapid cooling to a temperature of from 25° F. to 40° F. to improve refrigerated shelf life. The chilled product is then filled and sealed in sterilized containers under aseptic or near sterile conditions. The refrigerated shelf life may be enhanced by freezing the packaged product for a finite period of time prior to placing it in refrigerated storage.

30 Claims, No Drawings

METHOD OF PRODUCING CHOLESTEROL-FREE EGG PRODUCTS WITH AN EXTENDED REFRIGERATED SHELF LIFE AND PRODUCTS PRODUCED THEREBY

This application is a file wrapper continuation of application Ser. No. 07/209,802 filed June 22, 1988 now abandoned.

BACKGROUND OF THE INVENTION

Due to the close relationship between high cholesterol intake and the serum cholesterol level in humans (a factor in coronary heart disease), reduction in egg consumption, which is perhaps the largest single food source of cholesterol, has become a commonly accepted dietary measure in order to curb this ailment. Commercially available egg substitutes containing low or no cholesterol are thus becoming increasingly popular. These products are generally made of egg white with or without the yolk. To improve their palatability and stability, flavoring, coloring, emulsifying, thickening, and other modifying agents are generally added. Such products without the yolk are sold either frozen or refrigerated. The two major frozen products are identified by the U.S. Registered Trademarks SCRAMBLERS ® and EGG BEATERS ®. The major refrigerated product is identified by the trademark SECOND NATURE ®. The frozen products normally do not require the use of preservatives; however, it is necessary to use preservatives for the refrigerated products. For example, the SECOND NATURE ® product is covered by U.S. Pat. No. 3,928,632, and the preservative is lactylate salt. Conventionally pasteurized egg products (typically heated to 140° F. for three and a half minutes) can generally remain edible only for one to two weeks under refrigeration without a preservative.

SUMMARY OF THE INVENTION

The instant invention involves a process and a product produced thereby for treating an egg white product so as to achieve the maximum bactericidal kill without appreciable loss of protein functionalities and thus significantly increase its refrigerated shelf life, without the use of preservatives. This is accomplished by subjecting the egg white product to turbulent flow at an elevated temperature which would otherwise cause the formation of coagulated protein. The heated egg white product is then held at this elevated temperature for a fixed period of time. This is then followed by a rapid cooling. The resultant egg white product then is preferably aseptically packaged for refrigerated storage. Even greater refrigerated shelf life may be obtained if the aseptically packaged egg white product is frozen for a finite period of time prior to being placed in refrigerated storage.

Eggs, particularly egg white, are susceptible to coagulation at high temperatures. The egg proteins irreversibly transform from a water soluble to an insoluble state by heat. Under normal conditions, egg white starts to coagulate below 140° F. Therefore, it is unexpected that the egg white based mixture described in this invention when subjected to processing can withstand severe thermal treatment at a temperature as high as 162° F. without inducing significant protein denaturation. Combination of the product composition and process conditions disclosed in this invention enables the continuous production of the desirable products without significant protein damage and coagulation in the processing line.

It is therefore an object of this invention to provide a process and a product produced thereby which greatly extends the refrigerated shelf life of egg white products.

It is a further object of this invention to improve the refrigerated shelf life of the egg white product produced by this process wherein the egg white product is frozen for a finite length of time prior to actual refrigeration.

These, together with other objects and advantages of the invention will become more readily apparent to those skilled in the art from the following detailed description.

DETAILED DESCRIPTION OF THE INVENTION

In order to apply the thermal treatment of the instant invention on an egg white product which can maximize the bactericidal effect with a minimum protein damage, i.e., thermal coagulation, it is necessary that the raw mixture be fed into the production line at a rate which can generate a turbulent flow of the material in the heating tubes.

It is assumed that when a Reynold's number (Re), which is defined by the following equation:

$$Re = \frac{\rho v D}{\eta}$$

Where,
$\rho$ = mixture's density, lb/ft$^3$
v = flow velocity, ft/sec
D = tube's inside diameter, ft
$\eta$ = mixture's viscosity, lb/ft-sec is greater than 4000, the flow is considered turbulent. Since turbulent flow is an essential element in maximizing the heat transfer as well as minimizing the protein aggregation (formation of coagulated specks), these factors must be carefully evaluated and predetermined in the thermal process. It is desirable, as indicated in the above equation, to have a fluid of low viscosity to flow through selected heat exchanger tubing at a high velocity. Although large tubing can result in a greater Re, the fluid's velocity will be correspondingly reduced at a given flow rate. This relationship can be illustrated by the following formula:

$$v = \frac{4Q}{D^2}$$

Where,
Q = flow rate Therefore, Re can also be expressed as:

$$Re = \frac{4\rho Q}{\pi \eta D}$$

As the flow rate increases and/or the tubing diameter decreases, a turbulent flow can more likely be generated for a specific fluid than otherwise. For example, when a pseudoplastic fluid, such as described in this invention, exhibiting an apparent viscosity of 5 cps at high shear rate is pumped at a rate of 3 gallons per minute into a tube with an ID of 0.5 inch, a Re=5171 is achieved. At this level, the flow is in the turbulent region.

Preferably the temperature gradient between the heating medium and the product being heated is maintained at a minimum in order to discourage coagulation on the surface of the heating tube and consequent fouling. A desired egg white product can be made by preheating the mixture first to 120°–140° F. and preferably at 120°–130° F. in a tubular, shell-and-tube, or plate heat exchanger and then homogenizing it at two stages, i.e., first at 1300 psi and then at 500 psi, before the final heating at 150°–162° F. and preferably at 160°–162° F. in tubular heat exchangers using hot water as the heating medium with turbulent flow of the liquid egg white product therein.

In order to assure a minimum of 9D thermal death effect on Salmonella (i.e., a 9 log cycle kill of the microorganism, which is commonly found in eggs; i.e., a 99.9999999% reduction of the Salmonella originally existing in the raw mix), the heated egg white product is thereafter held at this high temperature while flowing through a holding tube for 45 to 60 seconds. The exact length of the holding tube is determined by the flow rate, tube size, and the time that the product is held in the tube.

It is a critical part of this invention that at the end of the holding period the egg white product be chilled rapidly to a temperature of from 25° F. to 40° F. to discourage the growth of the micro-organisms that survive the thermal treatment in order to obtain the maximum expected shelf life. Chilling of the product can be accomplished either on-line or in package. It is preferred, however, that it be carried out on-line continuously. To achieve that, a series of heat exchangers are employed to lower the product's temperature from 162° F. to 25°–40° F. in as short a period of time as practically possible. An additional benefit of this cooling is the minimization of protein denaturation.

The chilled product is then filled and sealed in sterilized containers under aseptic or near sterile conditions. The discharged products in containers are immediately stored under refrigeration and distributed also under refrigeration.

Preferably, in order to enhance shelf life, the product may be frozen for one to two weeks prior to distribution on refrigerated shelves. This results in an enhancement of the product's refrigerated shelf life by at least 30 percent.

The product produced by this process is enhanced if the starting material utilizes a specially blended mixture consisting of 70–99% liquid egg white, up to 4% non-fat dry milk, up to 2% starch, up to 5% vegetable oil as well as vitamins, flavoring, and coloring agents. Up to 2% calcium caseinate may also be added. The preferred range of liquid egg white is 78–95%. In this range the finished products yield cooking quality and functionalities most closely resembling those of natural eggs. Liquid egg white, either fresh or pasteurized, that contains no more than 3 mg cholesterol per 100 g of the raw material can be used as a starting material. By adding up to 2% calcium caseinate and/or 4% non-fat dry milk, the protein content and the flavor profile of the product are further improved.

The addition of starch, less than 2% by weight, provides a means for viscosity adjustment. The optimal rheological properties of the product include the two characteristics, namely, (1) a low apparent viscosity (e.g., less than 10 cps) at a high shear rate mimicking the processing conditions, and (2) a modestly high apparent viscosity (e.g., 100–300 cps) at a low shear rate simulating conditions at the user's end. The pseudoplastic behavior of the mixture aids the development of a turbulent flow in the heat exchanger tubes facilitating heat transfer during thermal processing. On the other hand, it is desirable that the finished products acquire a rich, yet easily pourable consistency. To accomplish this, a starch level at 1–2% is preferred. In addition, the starch acts to bind water and thus reduces water separation, increases freezer-thaw stability, and decreases water activity in a food system. Therefore, the incorporation of starch in the mixture serves multiple purposes.

Vegetable oils, such as corn oil, soybean oil, olive oil, peanut oil, etc., can be used either singly or in combination, in the mixture to yield the desirable eating and nutritional qualities. Up to 5% of such oils can be incorporated and homogeneously dispersed in the product to resemble the whole egg, replacing it in scrambling, baking, and other food preparations. To further improve the palatability and appearance of the product, flavoring (e.g., dairy flavors), coloring (e.g., creamy yellow) agents and vitamins (e.g., $\beta$-carotene, ascorbic acid) are added.

Ascorbic and/or citric acid are used to adjust the mixture's pH to 6.5 to 7.5, preferably 7.0–7.4. The pH adjustment not only facilitates the thermal bacterial kill, but also aids in preventing discoloration (i.e., greening) of the egg product upon cooking and prolonged heating. Besides the acids, aluminum sulfate may also be added (approximately 0.03%) along with starch, oil, and emulsifiers in the mixture. These ingredients are believed to increase the egg white's resistance to thermal denaturation. Consequently, the egg white in the mixture can tolerate a more severe heat treatment without much coagulation in the process.

The packaged products, when kept at 40° F. or below, have a shelf life exceeding seven months. At elevated storage temperatures, however, the shelf life will be considerably decreased. For example, at 50° F. the product was found to be unacceptable after ten weeks. On the other hand, if the products are subjected to freezing for one to two weeks immediately after packaging, their refrigerated shelf life can be further extended.

Example 1

An egg white based mixture with the following compositions (in percentage by weight) was blended and kept at refrigerated temperature.

| Ingredients | Percentage by Weight |
| --- | --- |
| Liquid Egg White | 83.9 |
| Water | 6.9 |
| Oil | 5.2 |
| NFDM | 2.0 |
| Starch | 1.0 |
| Flavoring | 0.68 |
| Aluminum Sulfate | 0.003 |
| Vitamins | 0.001 |

The mixture had a pH of 7.4–8.0 and was adjusted to pH 7.0 by using a 25% citric acid solution. It was then pumped through a thermal processing system at 25 lb. per minute (3 gallons per minute) and preheated in a tubular heat exchanger from 40° F. to 120° F. After preheating, it was homogenized at two stages, i.e., 1300 psi and 500 psi, prior to final heating. The final heating of the mixture from 120° F. to 162° F. was accomplished by using two tubular heat exchangers in series. These heat exchangers, as well as the preheater, used hot water as its heating medium. In order to precisely control the product temperature and the temperature gradient, particularly at the final heating stage, the temperature of the water medium was closely monitored and controlled. After the predetermined final product temperature was reached, the product was allowed to flow through a tube for 45 seconds before being chilled in a series of heat exchangers. The product temperature was then brought down to below 40° F. The chilled product was filled and sealed in sterilized containers in a near sterile chamber. The packaged products were refrigerated and gave a shelf life exceeding twenty-eight weeks at 40° F. and ten weeks at 50° F. The percentage of water soluble protein n the product, as determined by a protein analysis, indicated a minimum denaturation had occurred. A cake baking test showed a comparable textural measurement as well, when compared with a frozen product with a similar composition, which had been subjected to a pasteurization process at 140° F.

While this invention has been described in its preferred embodiment, it is to be appreciated that variations therefrom may be made without departing from the true scope and spirit of the invention.

What is claimed:

1. A method of treating a substantially cholesterol-free egg white product to improve its refrigerated shelf life which comprises heating said egg white product to a temperature of from approximately 150° F. to approximately 162° F., said heating occurring while said egg white product is transported through a heat exchanger at a velocity sufficient to create turbulent flow of said egg white product, holding said egg white product for from 45 to 60 seconds at said temperature and immediately thereafter cooling said egg white product to a temperature of from 25°–40° F. in as short a period of time as is possible, whereby the growth of micro-organisms that survive the thermal treatment is discouraged so as to obtain the maximum shelf life of the finished product.

2. The method of claim 1 wherein said egg white product is preheated to a temperature of from 120° F.–140° F. and then homogenized prior to being heated to a temperature of 162° F.

3. The method of claim 1 wherein said egg white product comprises liquid egg white, starch, and oil.

4. The method of claim 3 wherein said liquid egg white is present from 70% to 99%.

5. The method of claim 3 wherein said starch is present in said egg white product in an amount up to 2%.

6. The method of claim 3 wherein said oil is present in said egg white product in an amount up to 5%.

7. The method of claim 4 wherein said egg white product has a pH of approximately 7.0 to 7.4.

8. The method of claim 7 wherein said egg white product additionally contains flavoring, coloring agents, and vitamins.

9. The method of claim 1 wherein said cooled egg white product is immediately aseptically packaged and frozen for a period of one to two weeks.

10. The method of claim 9 wherein said egg white product comprises liquid egg white, starch, and oil.

11. The method of claim 10 wherein said liquid egg white is present from 70% to 99%.

12. The method of claim 10 wherein said starch is present in said egg white product in an amount up to 2%.

13. The method of claim 10 wherein said oil is present in said egg white product in an amount up to 5%.

14. The method of claim 9 wherein said egg white product has a pH of approximately 7.0 to 7.4.

15. The method of claim 14 wherein said egg white product additionally contains flavoring, coloring agents, and vitamins.

16. A substantially cholesterol-free egg white product with an extended refrigerated shelf life prepared by treating an egg white product by heating said egg white product to a temperature of from approximately 150° F. to approximately 162° F., said heating occurring while said egg white product is transported through a heat exchanger at a velocity sufficient to create turbulent flow of said egg white product, holding said egg white product for from 45 to 60 seconds at said temperature and immediately thereafter cooling said egg white product to a temperature of from 25° F.–40° F. in as short a period of time as is possible, whereby the growth of micro-organisms that survive the thermal treatment is discouraged so as to obtain the maximum shelf life of the finished product.

17. The product of claim 16 wherein said egg white product is preheated to a temperature of from 120° F.–140° F. and homogenized prior to being heated to a temperature of 162° F.

18. The product of claim 16 wherein said egg white product comprises liquid egg white, starch and oil.

19. The product of claim 18 wherein said liquid egg white is present in said egg white product from 70% to 99%.

20. The product of claim 18 wherein said starch is present in said egg white product in an amount up to 2%.

21. The product of claim 18 wherein said oil is present in said egg white product in an amount up to 5%.

22. The product of claim 19 wherein said egg white product has a pH of approximately 7.0 to 7.4.

23. The product of claim 22 wherein said egg white product additionally contains flavoring, coloring agents, and vitamins.

24. The product of claim 16 wherein said cooled egg white product has been immediately aseptically packaged and frozen for a period of one to two weeks.

25. The product of claim 24 wherein said egg white product comprises liquid egg white, starch, and oil.

26. The product of claim 25 wherein said liquid egg white is present from 70% to 99%.

27. The product of claim 25 wherein said starch is present in an amount up to 2%.

28. The product of claim 25 wherein said oil is present in an amount up to 5%.

29. The product of claim 24 wherein said egg white product has a pH of approximately 7.0 to 7.4.

30. The product of claim 29 wherein said egg white product additionally contains flavoring, coloring agents, and vitamins.

* * * * *